US009895098B2

(12) United States Patent
Ishikawa et al.

(10) Patent No.: US 9,895,098 B2
(45) Date of Patent: Feb. 20, 2018

(54) OPTICAL BIOMETRIC SYSTEM AND METHOD FOR USING SAME

(75) Inventors: Akihiro Ishikawa, Kyoto (JP); Yoshihiro Inoue, Kyoto (JP); Takashi Amita, Kyoto (JP); Satoru Kohno, Fuchu (JP); Haruhide Udagawa, Kyoto (JP); Yoshinori Masuda, Kyoto (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 551 days.

(21) Appl. No.: 14/391,656

(22) PCT Filed: May 11, 2012

(86) PCT No.: PCT/JP2012/062223
§ 371 (c)(1),
(2), (4) Date: Oct. 9, 2014

(87) PCT Pub. No.: WO2013/168294
PCT Pub. Date: Nov. 14, 2013

(65) Prior Publication Data

US 2015/0065890 A1 Mar. 5, 2015

(51) Int. Cl.
*A61B 5/00* (2006.01)
*A61B 5/026* (2006.01)

(52) U.S. Cl.
CPC .......... *A61B 5/4064* (2013.01); *A61B 5/0062* (2013.01); *A61B 5/0064* (2013.01); (Continued)

(58) Field of Classification Search
CPC .... A61B 5/4064; A61B 5/0062; A61B 5/0064
See application file for complete search history.

(56) References Cited

U.S. PATENT DOCUMENTS

2007/0083097 A1* 4/2007 Fujiwara .............. A61B 5/0059 600/407

FOREIGN PATENT DOCUMENTS

JP 2001-337033 A 12/2001
JP 2009-136434 A 6/2009
(Continued)

OTHER PUBLICATIONS

Francesco Fabbri, et al., "Optical measurements of absorption changes in two-layered diffusive media" Phys. Med. Biol., 2004, pp. 1183-1201, vol. 49.
(Continued)

*Primary Examiner* — Joseph Dietrich
(74) *Attorney, Agent, or Firm* — Sughrue Mion, PLLC

(57) ABSTRACT

An optical biometric system (1) is characterized by being provided with: a first received light amount information acquisition unit (25) which acquires skin blood flow data relating to a skin blood flow in a wide range of the scalp of a subject by controlling the transmission/reception of light to/from a light transmission/reception unit (30) using a wide-range control table; and a selection control table creation unit (24) which causes a storage unit (23) to store a selection control table for acquiring X pieces of first received light amount information (ΔA1) selected from among N pieces of first received light amount information (ΔA1), and in that when acquiring multiple pieces of measurement data relating to the brain activity in a predetermined range of the brain of the subject by controlling the transmission/reception of light to/from the light transmission/reception unit (30) using a control table, a light transmission/reception control unit (21) acquires skin blood flow data relating to a skin blood flow in a predetermined position of the scalp of the subject by controlling the transmission/
(Continued)

reception of light to/from the light transmission/reception unit (30) using the selection control table.

2 Claims, 12 Drawing Sheets

(52) U.S. Cl.
CPC .......... *A61B 5/0261* (2013.01); *A61B 5/6814* (2013.01); *A61B 5/0042* (2013.01); *A61B 2562/046* (2013.01); *A61B 2562/066* (2013.01)

(56) References Cited

FOREIGN PATENT DOCUMENTS

| | | | |
|---|---|---|---|
| JP | 2010-240298 | A | 10/2010 |
| JP | 2012-032204 | A | 2/2012 |
| WO | 2012/005303 | A1 | 1/2012 |

OTHER PUBLICATIONS

Rolf B. Saager, et al., "Direct characterization and removal of interfering absorption trends in two-layer turbid media," J. Opt. Soc. Am. A, Sep. 2005, pp. 1874-1882, vol. 22, No. 9.
International Search Report for PCT/JP2012/062223 dated Jun. 5, 2012.

* cited by examiner

FIG. 4

| Time light is on (msec) | 5 | 5 | 5 | 5 | 5 | 5 | 5 | 5 | 5 | 5 | 5 | 5 | 5 | 5 | 5 | 5 | 5 | 5 | 5 | 5 | 5 | 5 | 5 | 5 | 5 |
|---|---|---|---|---|---|---|---|---|---|---|---|---|---|---|---|---|---|---|---|---|---|---|---|---|---|
| Light transmitting probe that has been turned on | T1 | | | T2 | | | T3 | | | T4 | | | T5 | | | T6 | | | T7 | | | T8 | | | – |
| Wavelengths (nm) | 780 | 805 | 830 | 780 | 805 | 830 | 780 | 805 | 830 | 780 | 805 | 830 | 780 | 805 | 830 | 780 | 805 | 830 | 780 | 805 | 830 | 780 | 805 | 830 | – |
| Light receiving probe that acquires data | | | | | | | | | | | | | | | | | | | | | | | | | |
| R1 | | S1 | | | S2 | | | S5 | | | | | | | | | | | | | | | | | DARK |
| R2 | | | | | S3 | | | | | | S7 | | | | | | | | | | | | | | DARK |
| R3 | | S4 | | | | | | S8 | | | | | | S11 | | | | | | | | | | | DARK |
| R4 | | | | | S6 | | | S9 | | | S10 | | | | | | S13 | | | | | | | | DARK |
| R5 | | | | | | | | S12 | | | | | | S15 | | | S16 | | | S19 | | | | | DARK |
| R6 | | | | | | | | | | | S14 | | | | | | S17 | | | | | | S21 | | DARK |
| R7 | | | | | | | | | | | | | | S18 | | | | | | S22 | | | | | DARK |
| R8 | | | | | | | | | | | | | | | | | S20 | | | S23 | | | S24 | | DARK |

FIG. 5

| Time light is on (msec) | 5 | 5 | 5 | 5 | 5 | 5 | 5 | 5 | 5 | 5 | 5 | 5 | 5 | 5 | 5 | 5 | 5 | 5 | 5 | 5 | 5 | 5 | 5 | 5 | 5 |
|---|---|---|---|---|---|---|---|---|---|---|---|---|---|---|---|---|---|---|---|---|---|---|---|---|---|
| Light transmitting probe that has been turned on | T1 | | | T2 | | | T3 | | | T4 | | | T5 | | | T6 | | | T7 | | | T8 | | | – |
| Wavelengths (nm) | 780 | 805 | 830 | 780 | 805 | 830 | 780 | 805 | 830 | 780 | 805 | 830 | 780 | 805 | 830 | 780 | 805 | 830 | 780 | 805 | 830 | 780 | 805 | 830 | – |
| Light receiving probe that acquires data | | | | | | | | | | | | | | | | | | | | | | | | | |
| B1 | | C1 | | | | | | | | | | | | | | | | | | | | | | | DARK |
| B2 | | | | | | | | C2 | | | | | | | | | | | | | | | | | DARK |
| B3 | | | | | C3 | | | | | | | | | | | | | | | | | | | | DARK |
| B4 | | | | | | | | | | | C4 | | | | | | | | | | | | | | DARK |
| B5 | | | | | | | | | | | | | | C5 | | | | | | | | | | | DARK |
| B6 | | | | | | | | | | | | | | | | | | | | C7 | | | | | DARK |
| B7 | | | | | | | | | | | | | | | | | C6 | | | | | | | | DARK |
| B8 | | | | | | | | | | | | | | | | | | | | | | | C8 | | DARK |

FIG. 6

| Time light is on (msec) | 5 | 5 | 5 | 5 | 5 | 5 | 5 | 5 | 5 | 5 | 5 | 5 | 5 | 5 | 5 | 5 | 5 | 5 | 5 | 5 | 5 | 5 | 5 | 5 | 5 |
|---|---|---|---|---|---|---|---|---|---|---|---|---|---|---|---|---|---|---|---|---|---|---|---|---|---|
| Light transmitting probe that has been turned on | | T1 | | | T2 | | | T3 | | | T4 | | | T5 | | | T6 | | | T7 | | | T8 | | - |
| Wavelengths (nm) | 780 | 805 | 830 | 780 | 805 | 830 | 780 | 805 | 830 | 780 | 805 | 830 | 780 | 805 | 830 | 780 | 805 | 830 | 780 | 805 | 830 | 780 | 805 | 830 | - |
| | Light receiving probe that acquires data | | | | | | | | | | | | | | | | | | | | | | | | |
| R1 | | S1 | | | S2 | | | S5 | | | | | | | | | | | | | | | | | DARK |
| R2 | | | | | S3 | | | | | | S7 | | | | | | | | | | | | | | DARK |
| R3 | | S4 | | | | | | S8 | | | | | | S11 | | | | | | | | | | | DARK |
| R4 | | | | | S6 | | | S9 | | | S10 | | | | | | S13 | | | | | | | | DARK |
| R5 | | | | | | | | S12 | | | | | | S15 | | | S16 | | | S19 | | | | | DARK |
| R6 | | | | | | | | | | | S14 | | | | | | S17 | | | | | | S21 | | DARK |
| R7 | | | | | | | | | | | | | | S18 | | | | | | S22 | | | | | DARK |
| R8 | | | | | | | | | | | | | | | | | S20 | | | S23 | | | S24 | | DARK |
| B3 | | | | | C3 | | | | | | | | | | | | | | | | | | | | DARK |
| B4 | | | | | | | | | | | C4 | | | | | | | | | | | | | | DARK |

OPTICAL BIOMETRIC SYSTEM AND METHOD FOR USING SAME

TECHNICAL FIELD

The present invention relates to an optical biometric system and a method for using the same, and in particular to an optical biometric system for measuring brain activity noninvasively.

BACKGROUND ART

In recent years, optical brain function imaging apparatuses for a simple noninvasive measurement using light have been developed in order to observe the state of brain activity. In these optical brain function imaging apparatuses, the brain is irradiated with near-infrared rays having three different wavelengths $\lambda_1$, $\lambda_2$ and $\lambda_3$ (780 nm, 805 nm and 830 nm) by means of light transmitting probes placed on the surface of the scalp of a subject, and at the same time, changes in the intensity of the near-infrared rays of the respective wavelengths (information on the amount of received light) $\Delta A(\lambda_1)$, $\Delta A(\lambda_2)$ and $\Delta A(\lambda_3)$ that have been emitted from the brain are respectively detected by the light receiving probes placed on the surface of the scalp.

Then, simultaneous equations are formed as shown in the relational expressions (1), (2) and (3) using a modified Beer Lambert law, for example, in order to find the product [oxyHb] of the change in the concentration of oxyhemoglobin in the brain blood flow and the optical path length as well as the product [deoxyHb] of the change in the concentration of deoxyhemoglobin and the optical path length from the thus-gained information on the amount of received light $\Delta A(\lambda_1)$, $\Delta A(\lambda_2)$ and $\Delta A(\lambda_3)$, and then these simultaneous equations are solved. Furthermore, the product ([oxyHb]+[deoxyHb]) of the change in the concentration of the total amount of hemoglobin and the optical path length is calculated from the product [oxyHb] of the change in the concentration of oxyhemoglobin in the brain blood flow and the optical path length as well as the product [deoxyHb] of the change in the concentration of deoxyhemoglobin and the optical path length.

$$\Delta A(\lambda_1)=E_O(\lambda_1)\times[\text{oxyHb}]+E_d(\lambda_1)\times[\text{deoxyHb}] \quad (1)$$

$$\Delta A(\lambda_2)=E_O(\lambda_2)\times[\text{oxyHb}]+E_d(\lambda_2)\times[\text{deoxyHb}] \quad (2)$$

$$\Delta A(\lambda_3)=E_O(\lambda_3)\times[\text{oxyHb}]+E_d(\lambda_3)\times[\text{deoxyHb}] \quad (3)$$

Here, $E_O(\lambda_m)$ is the light absorbance coefficient of oxyhemoglobin for light having a wavelength $\lambda_m$, and $E_d(\lambda_m)$ is the light absorbance coefficient of deoxyhemoglobin for light having a wavelength $\lambda_m$.

The relationship between the measurement points and the distance (channel) between a pair of a light transmitting probe and a light receiving probe is described below. FIGS. 9(*a*) and 9(*b*) are diagrams showing the relationship between a measurement point and a pair of a light transmitting probe and a light receiving probe. A light transmitting probe 12 is pressed against a light transmitting point T on the surface of the scalp of a subject, and at the same time, a light receiving probe 13 is pressed against a light receiving point R on the surface of the scalp of the subject. Thus, light is emitted from the light transmitting probe 12, and at the same time, light released from the surface of the scalp enters into the light receiving probe 13. Light that has passed through the banana-shaped portion (measurement region) after being emitted from the light transmitting point T on the surface of the scalp reaches the light receiving point R on the surface of the scalp. That is to say, light passes through blood vessels in the skin in the vicinity of the light transmitting point T, blood vessels in the brain, and blood vessels in the skin in the vicinity of the light receiving point R.

Thus, cases where the distance (channel) between the light transmitting probe 12 and the light receiving probe 13 is a short distance r1 or a long distance r2 have been disclosed in order to acquire information on the amount of received light ΔA that had passed through blood vessels only in the brain (see Patent Document 1 and Non-Patent Document 1). FIG. 10 is a cross-sectional diagram showing the relationship between a reference probe 14 having a short distance r1 vis-à-vis the light transmitting probe 12, a light receiving probe 13 having a long distance r2 vis-à-vis the light transmitting probe 12, and the measurement point. As a result, the information on the amount of received light ΔA2 that has passed through blood vessels in the skin in the vicinity of the light transmitting point T, blood vessels in the brain, and blood vessels in the skin in the vicinity of the light receiving point R2 is acquired from the channel with a long distance r2, and at the same time, the information on the amount of received light ΔA1 that has passed through blood vessels on in the skin in the vicinity of the light transmitting point T (blood vessels in the skin in the vicinity of the light receiving point R1) is acquired from the channel with a short distance r1.

Then, the information on the amount of received light ΔA that has passed through blood vessels only in the brain is found using formula (4) from the thus-gained information on the amount of received light ΔA1 and ΔA2.

$$\Delta A=\Delta A2--K\Delta A1 \quad (4)$$

It is necessary to determine the coefficient K in order to find the information on the amount of received light ΔA in formula (4), and a calculation method for calculating this coefficient A has been disclosed (see Non-Patent Document 2). According to this calculation method, the coefficient K is calculated using the least square error.

In addition, a near-infrared spectrometer, for example, is used in optical brain function imaging apparatuses in order to measure the product [oxyHb] of the change in the concentration of oxyhemoglobin and the optical path length, the product [deoxyHb] of the change in the concentration of deoxyhemoglobin and the optical path length, and the product ([oxyHb]+[deoxyHb]) of the change in the concentration of total hemoglobin and the optical path length, respectively (see Patent Document 2).

FIG. 11 is a block diagram schematically showing an example of the configuration of a conventional near-infrared spectrometer. A near-infrared spectrometer 101 is provided with a light source 2 for emitting light, a light source driving mechanism 4 for driving the light source 2, a photodetector 3 for detecting light, an A/D converter 5, a light transmission/reception control unit 121, an analysis control unit 122 and a memory (storage unit) 123, and at the same time is provided with eight light transmitting probes 12, eight light receiving probes 13, a display 26 having a monitor screen 26*a* and the like, as well as a keyboard (input apparatus) 27.

The light source driving mechanism 4 chives the light source 2 using a drive signal that has been inputted from the light transmission/reception control unit 121. The light source 2 consists of semiconductor lasers LD1, LD2 and LD3 that can emit near-infrared rays having three different wavelengths $\lambda_1$, $\lambda_2$ and $\lambda_3$, for example.

The photodetector 3 is a detector that outputs a light reception signal (information on the amount of received light) $\Delta A(\lambda_1)$, $\Delta A(\lambda_2)$ and $\Delta A(\lambda_3)$ to the light transmission/reception control unit 121 via the A/D converter 5 by detecting the respective near-infrared rays and includes a photomultiplier tube, for example.

In this near-infrared spectrometer 101, a holder (light transmission/reception unit) 130 is used in order for the eight light transmitting probes 12 and the eight light receiving probes 13 to make contact with the surface of the scalp of a subject in a predetermined arrangement. FIG. 12 is a plan diagram showing an example of the holder 130 into which eight light transmitting probes and eight light receiving probes are inserted.

Light transmitting probes $\mathbf{12}_{T1}$ to $\mathbf{12}_{T8}$ and light receiving probes $\mathbf{13}_{R1}$ to $\mathbf{13}_{R8}$ are alternately arranged in a four-by-four grid in the longitudinal and lateral directions. Here, a second set distance r2 that is the distance (channel) between each light transmitting probe $\mathbf{12}_{T1}$ to $\mathbf{12}_{T8}$ and each light receiving probe $\mathbf{13}_{R1}$ to $\mathbf{13}_{R8}$ is 30 mm. As a result, information on the amount of received light $\Delta A(\lambda_1)$, $\Delta A(\lambda_2)$ and $\Delta A(\lambda_3)$ is gained for 24 measurement points in the brain.

In this matrix of eight light transmitting probes $\mathbf{12}_{T1}$ to $\mathbf{12}_{T8}$ and eight light receiving probes $\mathbf{13}_{R1}$ to $\mathbf{13}_{R8}$, it is necessary to adjust the timing in which light is emitted from the light transmitting probes 12 and the timing in which light is received by the light receiving probes 13 so that one light receiving probe 13 receives light emitted from one light transmitting probe 12 instead of simultaneously receiving light emitted from a number of light transmitting probes 12. In order to do so, a control table storage region 123*a* in the memory 123 stores a control table for indicating the timing in which the light source 2 emits light and the timing in which the photodetector 3 detects the light.

On the basis of the control table stored in the control table storage region 123*a*, the light transmission/reception control unit 121 outputs a drive signal for transmitting light to one light transmitting probe 12 at a predetermined time to the light source driving mechanism 4, and at the same time allows the photodetector 3 to detect a light reception signal (information on the amount of received light) that has been received by a light receiving probe 13, and then stores the signal in the data storage region 123*b*.

FIG. 4 shows an example of a control table. According to this control table, the light transmitting probe $\mathbf{12}_{T1}$ is made to transmit light having a wavelength of 780 nm during the first five milliseconds, the light transmitting probe $\mathbf{12}_{T1}$ is made to transmit light having a wavelength of 805 nm during the next five milliseconds, the light transmitting probe $\mathbf{12}_{T1}$ is made to transmit light having a wavelength of 830 nm during the following five milliseconds, the light transmitting probe $\mathbf{12}_{T2}$ is made to transmit light having a wavelength of 780 nm during the next five milliseconds, and so on, and thus, light transmitting probes $\mathbf{12}_{T1}$ to $\mathbf{12}_{T8}$ are made to transmit light having three different wavelengths sequentially according to a predetermined timing. Though eight light receiving probes $\mathbf{13}_{R1}$ to $\mathbf{13}_{R8}$ detect a light reception signal whenever any one of the light transmitting probes $\mathbf{12}_{T1}$ to $\mathbf{12}_{T8}$ is made to transmit light, only a light reception signal detected by a predetermined light receiving probe $\mathbf{13}_{R1}$ to $\mathbf{13}_{R8}$ according to a predetermined timing is stored in the data storage region 123*b* in the memory 123. Concretely, the light reception signals from the light receiving probe $\mathbf{13}_{R1}$ and the light receiving probe $\mathbf{13}_{R3}$ that have detected light from the light transmitting probe $\mathbf{12}_{T1}$ are stored in the data storage region 123*b*, the light reception signals from the light receiving probe $\mathbf{13}_{R1}$, the light receiving probe $\mathbf{13}_{R2}$ and the light receiving probe $\mathbf{13}_{R4}$ that have detected light from the light transmitting probe $\mathbf{12}_{T2}$ are stored in the data storage region 123*b*, and likewise, the light reception signals from the predetermined light receiving probes $\mathbf{13}_{R1}$ to $\mathbf{13}_{R8}$ that have detected light according to a predetermined timing are stored in the data storage region 123*b*. As a result, a total of 24 pieces of information on the amount of received light $\Delta A2(\lambda_1)$, $\Delta A2(\lambda_2)$ and $\Delta A2(\lambda_3)$ is collected.

On the basis of the 24 pieces of information on the amount of received light $\Delta A2(\lambda_1)$, $\Delta A2(\lambda_2)$ and $\Delta A2(\lambda_3)$, the analysis control unit 122 finds the product [oxyHb] of the change in the concentration of oxyhemoglobin and the optical path length, the product [deoxyHb] of the change in the concentration of deoxyhemoglobin and the optical path length, and the product ([oxyHb]+[deoxyHb]) of the change in the concentration of total hemoglobin and the optical path length as 24 pieces of measurement data from the intensity of the light that has passed through the optical paths having the respective wavelengths (wavelength of light absorbed by oxyhemoglobin and wavelength of light absorbed by deoxyhemoglobin) using the relational expressions (1), (2) and (3). As a result, 24 pieces of measurement data are displayed on the monitor screen 26*a* so that doctors, technicians and the like can observe the data. For example, an image for each piece of measurement data is displayed in each of the 24 predetermined locations on the image of the surface of the brain in such a manner that each piece of measurement data is expressed as a color that corresponds to the numeric value of the product [oxyHb] of the change in the concentration of oxyhemoglobin and the optical path length at a certain measurement time t.

PRIOR ART DOCUMENTS

Patent Documents

Patent Document 1: Japanese Unexamined Patent Publication 2009-136434

Patent Document 2: Japanese Unexamined Patent Publication 2001-337033

Non-Patent Documents

Non-Patent Document 1: Rolf B. Saager and Andrew J. Berger, "Direct characterization and removal of interfering absorption trends in two-layer turbid media," J. Opt. Soc. Am. A/Vol. 22, No. 9/September 2005.

Non-Patent Document 2: Francesco Fabbri, Angelo Sassaroli, Michel E. Henry, and Sergio Fantini, "Optical measurements of absorption changes in two-layered diffusive media," Phys. Med. Biol. 49 (2004) 1183-1201.

SUMMARY OF THE INVENTION

Problem to be Solved by the Invention

Though the information on the amount of received light $\Delta A$ is calculated in accordance with a calculation method using the information on the amount of received light $\Delta A1$ and $\Delta A2$ as well as the coefficient K as described above, the calculation is carried out by taking the combination of the pairs of the light transmitting probes 12 and the light receiving probes 13 into consideration, and the combinations of a number of light transmitting probes $\mathbf{12}_{T1}$ to $\mathbf{12}_{T8}$ and a number of light receiving probes $\mathbf{13}_{R1}$ to $\mathbf{13}_{R8}$, such as in the above-described holder 130 in the optical brain function imaging apparatus 101, are not taken into consideration. That is to say, the information on the amount of received light ΔA concerning a number of (24) measurement points on the brain is not calculated.

Though it is possible to provide a number of (8, for example) reference probes 14 having a short distance r2 vis-à-vis the light transmitting probe for all the combinations of the light transmitting probes $\mathbf{12}_{T1}$ to $\mathbf{12}_{T8}$ and the light receiving probes $\mathbf{13}_{R1}$ to $\mathbf{13}_{R8}$ in order to calculate the information on the amount of received light ΔA in accordance with the above-described calculation method, it is costly to provide eight reference probes 14.

Means for Solving Problem

In order to solve the above-described problem, the present inventors tried to find a method according to which the information on the amount of received light that has passed through blood vessels only in a number of measurement points on the brain can be examined without providing a number of (8, for example) reference probes 14. Thus, the inventors decided to acquire skin blood flow data on the blood flow in the skin in a predetermined range of the scalp of a subject before the measurement data in the predetermined range of the brain of the subject is acquired so as to find which pieces of skin blood flow data are in necessary points (2, for example) while observing the skin blood flow data. After that, the inventors acquired skin blood flow data in necessary points (2, for example) when measurement data in a predetermined range of the brain of a subject was acquired. That is to say, the inventors found a method according to which a pretest for acquiring skin blood flow data in a predetermined range of the scalp of a subject is first performed by detecting light using a great number of reference probes 14, and a small number of reference probes 14 are selected while observing the skin blood flow data in the pretest, and after that, the main test for acquiring measurement data in the predetermined range of the brain of the subject is carried out while acquiring the skin blood flow data in the necessary points (2, for example) on the scalp of the subject by detecting light using the small number of reference probes 14 and the light receiving probes 13.

Thus, the optical biometric system according to the present invention is an optical biometric system having: a light transmission/reception unit having a number of light transmitting probes placed on the surface of the scalp of a subject and a number of light receiving probes placed on the surface of the scalp, where each light receiving probe is located a second set distance r2 away from a light transmitting probe; and a light transmission/reception control unit for acquiring a number of pieces of measurement data on the brain activity in a predetermined range of the brain of the subject by acquiring a number of pieces of second information on the amount of received light ΔA2 between the light transmitting probes and the light receiving probes, wherein it is possible to place N reference probes at points a first set distance r1, which is shorter than the second set distance r2, away from a light transmitting probe in the above-described light transmission/reception unit, the optical biometric system further comprises a unit for acquiring first information on the amount of received light for acquiring skin blood flow data on the blood flow in the skin in a wide range of the scalp of the above-described subject by acquiring N pieces of first information on the amount of received light ΔA1 between the light transmitting probes and the reference probes, X pieces of first information on the amount of received light ΔA1 is selected from among the N pieces of first information on the amount of received light ΔA1 after a pretest for gaining skin blood flow data on the blood flow in the skin in a wide range of the scalp of the above-described subject has been carried out, and the above-described light transmission/reception control unit carries out a main test for acquiring skin blood flow data on the blood flow in the skin in a predetermined point on the scalp of the above-described subject by acquiring X pieces of first information on the amount of received light ΔA1 when a number of pieces of measurement data on the brain activity in a predetermined range of the brain of the subject is acquired by acquiring a number of pieces of second information on the amount of received light ΔA2 between the light transmitting probes and the light receiving probes.

Here, the "second set distance r2" is a distance for acquiring information on the amount of received light that has passed through blood vessels in the skin in the vicinity of the light transmitting point T, blood vessels in the brain, and blood vessels in the skin in the vicinity of the light receiving point R, while the "first set distance r1" is a distance for acquiring information on the amount of received light that has passed through vessels in the skin in the vicinity of the light transmitting point T or the light receiving point R.

In addition, the "predetermined range in the brain of a subject" is any range of the brain to be measured, which is determined by the size of the light transmission/reception unit and the like; the "wide range of the scalp of a subject" is any range of the scalp, which is determined by the size of the light transmission/reception unit and the like; and the "predetermined point on the scalp of a subject" is a point for measuring blood vessels in other parts of the brain, and for example, a point for measuring main arteries or main veins within two centimeters from the scalp or arteries in the vicinity of the light transmission/reception unit or veins in the vicinity of the light transmission/reception unit, which is an appropriate point for acquiring skin blood flow data according to the present invention.

Effects of the Invention

As described above, in accordance with the optical biometric system according to the present invention, a doctor, technician or the like carries out a pretest for examining a number of pieces of skin blood flow data, and therefore, necessary pieces of skin blood flow data can be selected, and as a result, a number of pieces of measurement data can be acquired in the main test after only necessary pieces of skin blood flow data have been acquired.

Other Means for Solving Problem and their Effects

The optical biometric system according to the present invention may further have: a storage unit for storing in advance a wide-range control table for acquiring N pieces of first information on the amount of received light ΔA1 between the light transmitting probes and the reference probes; and a selection control table creation unit for storing a selection control table for acquiring X pieces of first information on the amount of received light ΔA1 in the storage unit, wherein the above-described unit for acquiring first information on the amount of received light gains skin blood flow data on the blood flow in the skin in a wide range of the scalp of the above-described subject by controlling the light transmission/reception for the above-described light transmission/reception unit using the wide-range control table, and the above-described light transmission/reception control unit acquires skin blood flow data on the blood flow in the skin in predetermined point on the scalp of the above-described subject by controlling the light transmission/reception for the above-described light transmission/reception unit using the above-described selection control table after the selection control table has been stored.

In addition, the method for using an optical biometric system according to the present invention is a method for using a optical biometric system having a light transmission/reception unit having a number of light transmitting probes placed on the surface of the scalp of a subject and a number of light receiving probes placed on the surface of the scalp, where each light receiving probe is located a second set distance r2 away from a light transmitting probe, and a light transmission/reception control unit for acquiring a number of pieces of measurement data on the brain activity in a predetermined range of the brain of the subject by acquiring a number of pieces of second information on the amount of received light ΔA2 between the light transmitting probes and the light receiving probes, where it is possible to place N reference probes at points a first set distance r1, which is shorter than the second set distance r2, away from a light transmitting probe in the above-described light transmission/reception unit, including: a pretest step of acquiring skin blood flow data on the blood flow in the skin in a wide range of the scalp of the above-described subject by acquiring N pieces of first information on the amount of received light ΔA1 between the light transmitting probes and the reference probes, a selection step of selecting X pieces of first information on the amount of received light ΔA1 from among the N pieces of first information on the amount of received light ΔA1, and a main test step of acquiring skin blood flow data on the blood flow in the skin in a predetermined point on the scalp of the above-described subject by acquiring X pieces of first information on the amount of received light ΔA1 when a number of pieces of measurement data on the brain activity in a predetermined range of the brain of the subject is acquired by acquiring a number of pieces of second information on the amount of received light ΔA2 between the light transmitting probes and the light receiving probes.

BRIEF DESCRIPTION OF THE DRAWINGS

FIG. 4 is an example of a control table;

FIG. 5 is an example of a wide-range control table;

FIG. 6 is an example of a selection control table;

PREFERRED EMBODIMENTS OF THE INVENTION

Embodiments of the present invention are described below in reference to the drawings. The present invention is not limited to the below-described embodiments, but rather includes various modifications as long as the gist of the present invention is not deviated from.

Figure 1:
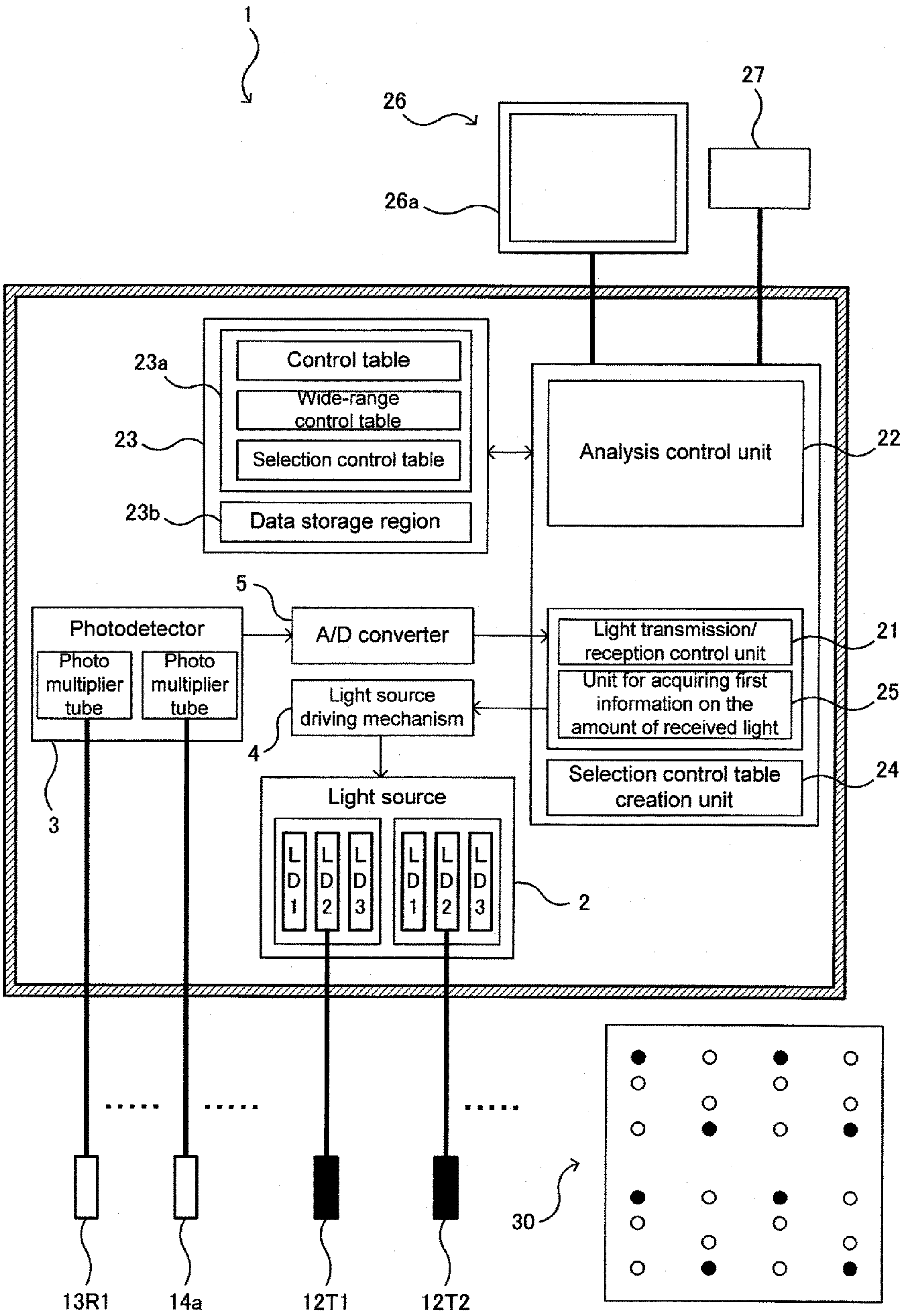
FIG. 1 is a block diagram schematically showing the configuration of the optical biometric apparatus according to one embodiment of the present invention.
Figure 2:
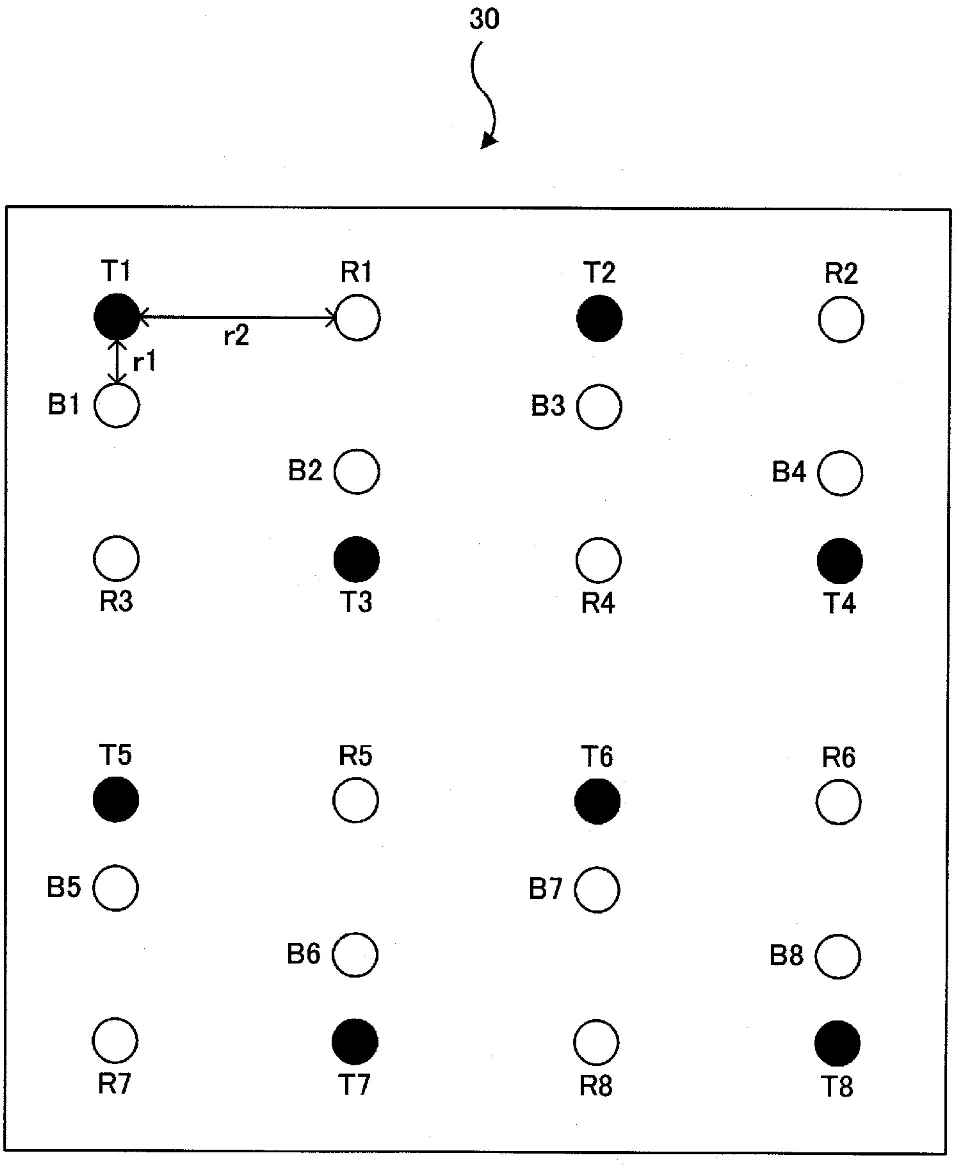
FIG. 2 is a plan diagram showing an example of a holder into which eight light transmitting probes, eight light receiving probes and eight reference probes are inserted.

FIG. 1 is a block diagram schematically showing the configuration of the optical biometric apparatus according to one embodiment of the present invention. FIG. 2 is a plan diagram showing an example of a holder (light transmission/reception unit) into which eight light transmitting probes, eight light receiving probes and eight reference probes are inserted. Here, the same symbols are attached to the components as in the near-infrared spectrometer 101.

An optical biometric apparatus (optical biometric system) 1 is provided with a light source 2 for emitting light, a light source driving mechanism 4 for driving the light source 2, a photodetector 3 for detecting light, an A/D converter 5, a light transmission/reception control unit 21, an analysis control unit 22, a selection control table creation unit 24, a unit for acquiring first information on the amount of received light 25, and a memory (storage unit) 23, and in addition is provided with eight light transmitting probes 12, eight light receiving probes 13, two (X<N) reference probes 14*a* and 14*b*, a display 26 having a monitor screen 26*a* and the like, and a keyboard (input apparatus) 27.

The light source 2 transmits light to one light transmitting probe 12 selected from among the eight light transmitting probes $\mathbf{12}_{T1}$ and $\mathbf{12}_{T8}$ in response to a drive signal that has been inputted from the light transmission/reception control unit 21. Near-infrared rays (light having three wavelengths, 780 nm, 805 nm and 830 nm, for example) are used as the above-described light.

The photodetector 3 individually detects the near-infrared rays that have been received by the eight light receiving probes $\mathbf{13}_{R1}$ to $\mathbf{13}_{R8}$ (light having three wavelengths, 780 nm, 805 nm and 830 nm, for example) so that eight pieces of second information on the amount of received light $\Delta A(\lambda_1)$, $\Delta A(\lambda_2)$ and $\Delta A(\lambda_3)$ are outputted to the light transmission/reception control unit 21, and at the same time individually detects the near-infrared rays that have been received by the two (X) light receiving probes 14 (light having three wavelengths, 780 nm, 805 nm and 830 nm, for example) so that first information on the amount of received light $\Delta A1_x(\lambda_1)$, $\Delta A1_x(\lambda_2)$ and $\Delta A1_x(\lambda_3)$ (x=1, 2) is outputted to the light transmission/reception control unit 21.

The holder 30 has through holes T1 to T8, R1 to R8 and B1 to B8 into which eight light transmitting probes $\mathbf{12}_{T1}$ to $\mathbf{12}_{T8}$, eight light receiving probes $\mathbf{13}_{R1}$ to $\mathbf{13}_{R8}$ and eight (N) reference probes $\mathbf{14}_{B1}$ to $\mathbf{14}_{B8}$ can be placed.

The through holes T1 to T8 into which the light transmitting probes $\mathbf{12}_{T1}$ to $\mathbf{12}_{T8}$ can be placed and the through holes R1 to R8 into which the light receiving probes $\mathbf{13}_{R1}$ to $\mathbf{13}_{R3}$ can be placed are arranged in a square grid shape so as to alternate in the row and column directions. Here, the second set distance r2 that is the distance (channel) between the through holes T1 to T8 into which the light transmitting probes $12_{T1}$ to $12_{T8}$ can be placed and the through holes R1 to R8 into which the light receiving probes $13_{R1}$ to $13_{R8}$ can be placed is 30 mm.

In addition, the through hole B1 into which the reference probe $14_{B1}$ can be placed is located between the through hole T1 into which the light transmitting probe $12_{T1}$ can be placed and the through hole R3 into which the light receiving probe $13_{R3}$ can be placed and is at the first set distance r1 away from the through hole T1 into which the light transmitting probe $12_{T1}$ can be placed, where the first set distance r1 that is the distance between the through hole T1 into which the light transmitting probe $12_{T1}$ can be placed and the through hole B1 into which the reference probe $14_{B1}$ can be placed is 10 mm. Furthermore, the respective through holes into which each reference probe 14 can be placed are the first set distance r1 away from a through hole into which each light transmitting probe 12 can be placed in such a manner that the through hole B2 into which the reference probe $14_{B2}$ can be placed is the first set distance r1 away from the through hole T3 into which the light transmitting probe $12_{T3}$ can be placed, and the through hole B3 into which the reference probe $14_{B3}$ can be placed is the first set distance r1 away from the through hole T2 into which the light transmitting probe $12_{T2}$ is placed.

In the memory 23, a control table for setting the manner of controlling the transmission/reception of light to/from the holder 30 in order to acquire 24 pieces of measurement data is stored in advance, and at the same time, a wide-range control table for setting the manner of controlling the transmission/reception of light to/from the holder 30 in order to acquire eight (N) pieces of skin blood flow data is stored in advance. Furthermore, the memory 23 has a control table storage region 23*a* for storing a selection control table that sets the manner of controlling the transmission/reception of light to/from the holder 30 in order to acquire two (X) pieces of skin blood flow data, and a data storage region 23*b* for storing a light reception signal (measurement data) and the like.

Figure 3:
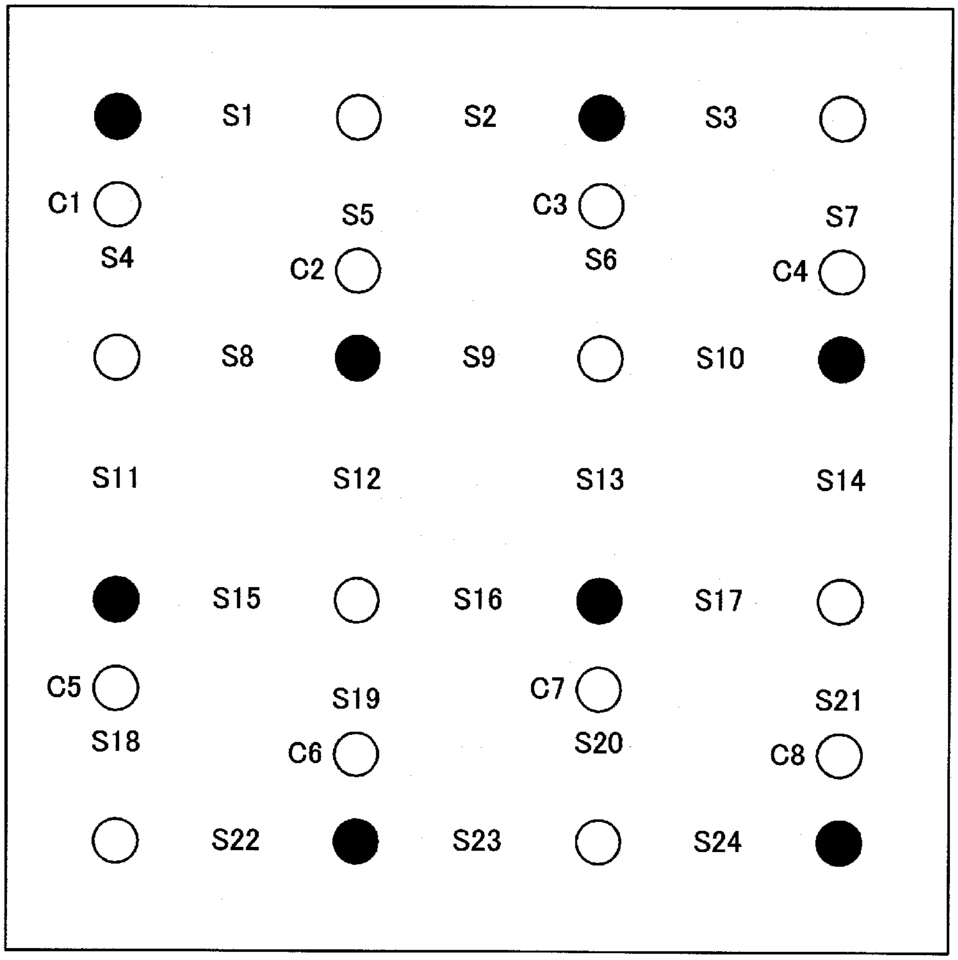
FIG. 3 is a diagram showing the points where information on the amount of received light can be gained.

FIG. 4 shows an example of a control table as described above. FIG. 3 is a diagram showing the locations at which information on the amount of received light can be gained. Here, the control table is used in the same manner as the control table in the near-infrared spectrometer 101, and therefore, the descriptions thereof are omitted.

FIG. 5 shows an example of the wide-range control table. According to this wide-range control table, one light transmitting probe 12 is made to transmit light sequentially according to a predetermined timing in such a manner that the light transmitting probe $12_{T1}$ is made to transmit light having a wavelength of 780 nm for the first five milliseconds, the light transmitting probe $12_{T1}$ is made to transmit light having a wavelength of 805 nm for the next five milliseconds, the light transmitting probe $12_{T1}$ is made to transmit light having a wavelength of 830 nm for the following five milliseconds, and the light transmitting probe $12_{T2}$ is made to transmit light having a wavelength of 780 nm for the next five milliseconds. At this time, a light reception signal is detected by eight reference probes $14_{B1}$ to $14_{B8}$ whenever any one light transmitting probe 12 is made to transmit light, and the light reception signal directed by a predetermined reference probe 14 according to a predetermined timing is stored in the data storage region 23*b* in the memory 23. Concretely, the light reception signal from a predetermined reference probe 14 that had detected light according to a predetermined timing is stored in the data storage region 23*b* in such a manner that the light reception signal from the reference probe $14_{B1}$ that had detected the light from the light transmitting probe $12_{T1}$ is stored in the data storage region 23*b*, and the light reception signal from the reference probe $14_{B2}$ that had detected the light from the light transmitting probe $12_{T3}$ is stored in the data storage region 23*b*. As a result, eight (N) pieces of first information on the amount of received light $\Delta A1_n(\lambda_1)$, $\Delta A1_n(\lambda_2)$ and $\Delta A1_n(\lambda_3)$ (n=1, 2 . . . 8) are collected in total.

FIG. 6 shows an example of the selection control table. Here, the method for creating a selection control table is described in detail in the following. According to this selection control table, two (X) reference probes 14 detect a light reception signal whenever any one light transmitting probe 12 is made to transmit light while the control table makes one light transmitting probe 12 transmit light sequentially according to a predetermined timing, and the light reception signal from a predetermined reference probe 14 that had detected the light in accordance with the predetermined timing is stored in the data storage region 23*b* in the memory 23. Concretely, the light reception signal from a predetermined reference probe 14 that had detected light according to a predetermined timing is stored in the data storage region 23*b* in such a manner that the light reception signal from the reference probe $14_{B3}$ that had detected the light from the light transmitting probe $12_{T3}$ is stored in the data storage region 23*b*, and the light reception signal from the reference probe $14_{B4}$ that had detected the light from the light transmitting probe $12_{T4}$ is stored in the data storage region 23*b*. As a result, two (X) pieces of first information on the amount of received light $\Delta A1_x(\lambda_1)$, $\Delta A1_x(\lambda_2)$ and $\Delta A1_x(\lambda_3)$ (x=1, 2) are collected in total.

When an input signal for acquiring eight (N) pieces of skin blood flow data is received, the unit for acquiring first information on the amount of received light 25 outputs a drive signal for transmitting light to one light transmitting probe 12 at a predetermined timing to the light source driving mechanism 4, and at the same time allows the photodetector 3 to detect a light reception signal (information on the amount of received light) that had been received by a reference probe 14 on the basis of the wide-range control table stored in the control table storage region 23*a*.

Concretely, the unit for acquiring first information on the amount of received light 25 allows one light transmitting probe 12 to transmit light sequentially according to a predetermined timing in such a manner that the light transmitting probe $12_{T1}$ is made to transmit light having a wavelength of 780 nm for the first five milliseconds, the light transmitting probe $12_{T1}$ is made to transmit light having a wavelength of 805 nm for the next five milliseconds, the light transmitting probe $12_{T1}$ is made to transmit light having a wavelength of 830 nm for the following five milliseconds, and the light transmitting probe $12_{T2}$ is made to transmit light having a wavelength of 780 nm for the next five milliseconds. At this time, the light reception signal from a predetermined reference probe $14_{B1}$ to $14_{B8}$ that had detected light according to a predetermined timing is stored in the data storage region 23*b* in the memory 23. As a result, eight (N) pieces of first information on the amount of received light $\Delta A1_n(\lambda_1)$, $\Delta A1_n(\lambda_2)$ and $\Delta A1_n(\lambda_3)$ (n=1, 2 . . . 8) are collected in total.

When an input signal for acquiring 24 pieces of measurement data is received (after the selection control table has been stored in the control table storage region 23*a*), the light transmission/reception control unit 21 outputs a drive signal for transmitting light to one light transmitting probe 12 at a predetermined time to the light source driving mechanism 4 on the basis of the control table and the selection control table stored in the control table storage region 23*a*, and at the same time allows the photodetector 3 to detect the light reception signals (information on the amount of received light) that had been received by the light receiving probes 13 and the reference probes 14.

Concretely, the light transmission/reception control unit 21 allows one light transmitting probe 12 to transmit light sequentially according to a predetermined timing in such a manner that the light transmitting probe $\mathbf{12}_{T1}$ is made to transmit light having a wavelength of 780 nm for the first five milliseconds, the light transmitting probe $\mathbf{12}_{T1}$ is made to transmit light having a wavelength of 805 nm for the next five milliseconds, the light transmitting probe $\mathbf{12}_{T1}$ is made to transmit light having a wavelength of 830 nm for the following five milliseconds, and the light transmitting probe $\mathbf{12}_{T2}$ is made to transmit light having a wavelength of 780 nm for the next five milliseconds. At this time, the light reception signals from a predetermined light receiving probe $\mathbf{13}_{R1}$ to $\mathbf{13}_{R8}$ and a predetermined reference probe $\mathbf{14}_{B1}$ to $\mathbf{14}_{B8}$ that had detected light according to a predetermined timing are stored in the data storage region 23*b* in the memory 23. As a result, 24 pieces of information on the amount of received light $\Delta A2\ (\lambda_1)$, $\Delta A2(\lambda_2)$ and $\Delta A2(\lambda_3)$ are collected in total, and at the same time, two (X) pieces of first information on the amount of received light $\Delta A1_x(\lambda_1)$, $\Delta A1_x(\lambda_2)$ and $\Delta A1_x(\lambda_3)$ (x=1, 2) are collected in total.

Figure 7:
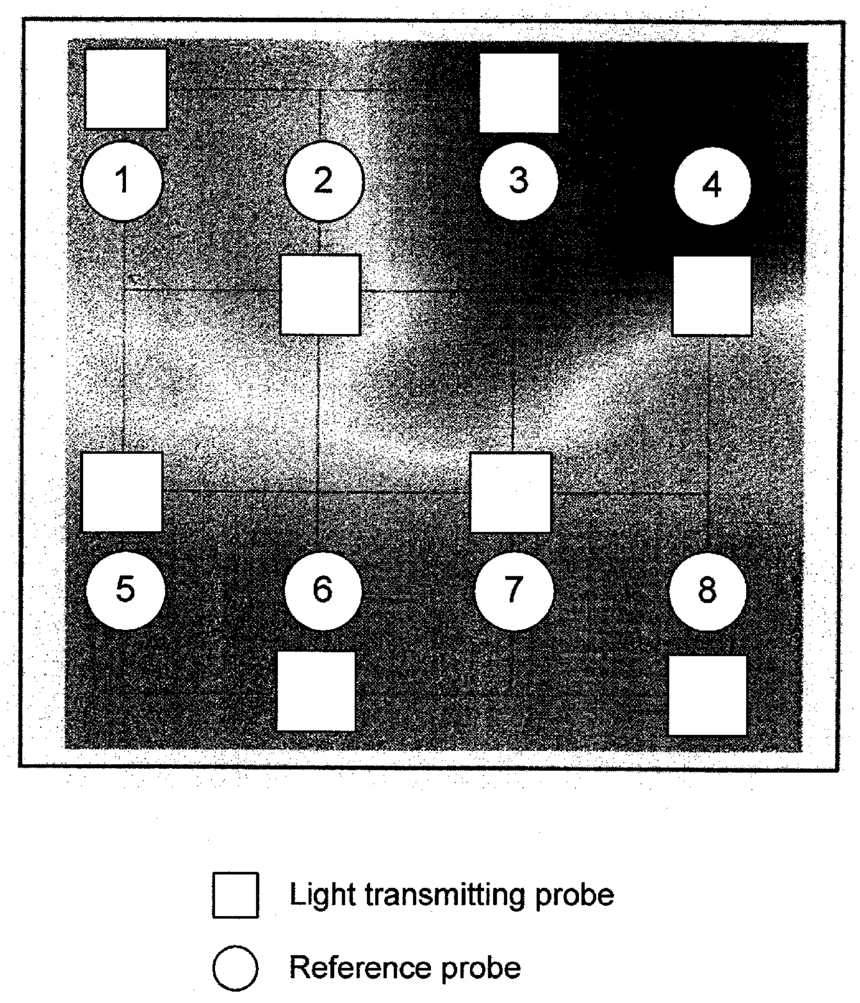
FIG. 7 is a diagram showing an image for displaying eight pieces of skin blood flow data.

When eight (N) pieces of skin blood flow data are acquired, the analysis control unit 22 finds the product [oxyHb] of the concentration of oxyhemoglobin and the optical path length, the product [deoxyHb] of the concentration of deoxyhemoglobin and the optical path length, and the product ([oxyHb]+[deoxyHb]) of the concentration of total hemoglobin and the optical path length as eight pieces of skin blood flow data from the intensity of light having each wavelength (wavelength of light absorbed by oxyhemoglobin and wavelength of light absorbed by deoxyhemoglobin) that has passed through blood vessels using the relational equations (1), (2) and (3) on the basis of the eight (N) pieces of first information on the amount of received light $\Delta A1_n(\lambda_1)$, $\Delta A1_n(\lambda_2)$ and $\Delta A1_n(\lambda_3)$ (n=1, 2 . . . 8). As a result, the monitor screen 26*a* displays an image of eight pieces of skin blood flow data in eight predetermined locations C1 to C8 on the image of the surface of the scalp as shown in FIG. 7. At this time, the skin blood flow data, for example, the products [oxyHb] of the change in the concentration of oxyhemoglobin and the optical path length at eight predetermined locations C1 to C8 at a certain measurement time t, is expressed with colors on the basis of a color table indicating the corresponding relationships between the numeric values and the colors. In addition, the predetermined eight locations C1 to C8 are middle points of curve sections connecting a light transmitting point T and a light receiving point B along the surface of the scalp of a subject so as to be at the shortest distance.

When 24 pieces of measurement data are acquired (after the selection control table has been stored in the control table storage region 23*a*), the analysis control unit 22 finds the product [oxyHb] of the concentration of oxyhemoglobin and the optical path length, the product [deoxyHb] of the concentration of deoxyhemoglobin and the optical path length, and the product ([oxyHb]+[deoxyHb]) of the concentration of total hemoglobin and the optical path length as 24 pieces of measurement data and two pieces of skin blood flow data from the intensity of light having each wavelength (wavelength of light absorbed by oxyhemoglobin and wavelength of light absorbed by deoxyhemoglobin) that has passed through blood vessels using the relational equations (1), (2) and (3) on the basis of the 24 pieces of second information on the amount of received light $\Delta A2\ (\lambda_1)$, $\Delta A2\ (\lambda_2)$ and $\Delta A2\ (\lambda_3)$ and two (X) pieces of first information on the amount of received light $\Delta A1_x(\lambda_1)$, $\Delta A1_x(\lambda_2)$ and $\Delta A1_x(\lambda_3)$ (x=1, 2).

The selection control table creation unit 24 creates a selection control table for acquiring two (X) pieces of skin blood flow data when a desired number (X) of pieces of skin blood data and their points of locations are selected from among the eight (N) pieces of skin blood flow data through an input operation with the keyboard 27, and then stores the selection control table in the control table storage region 23*a*.

At this time, the doctor, technician or the like selects X pieces of skin blood flow data as a result of the setting on the image displayed on the monitor screen 23*a* through an input operation with the keyboard 27, for example, and thus selects the necessary skin blood flow data from among the eight pieces of skin blood flow data on the image displayed as shown in FIG. 7. As a result, the skin blood flow data for the skin blood flow through necessary portions can be prevented from being missed.

Figure 8:
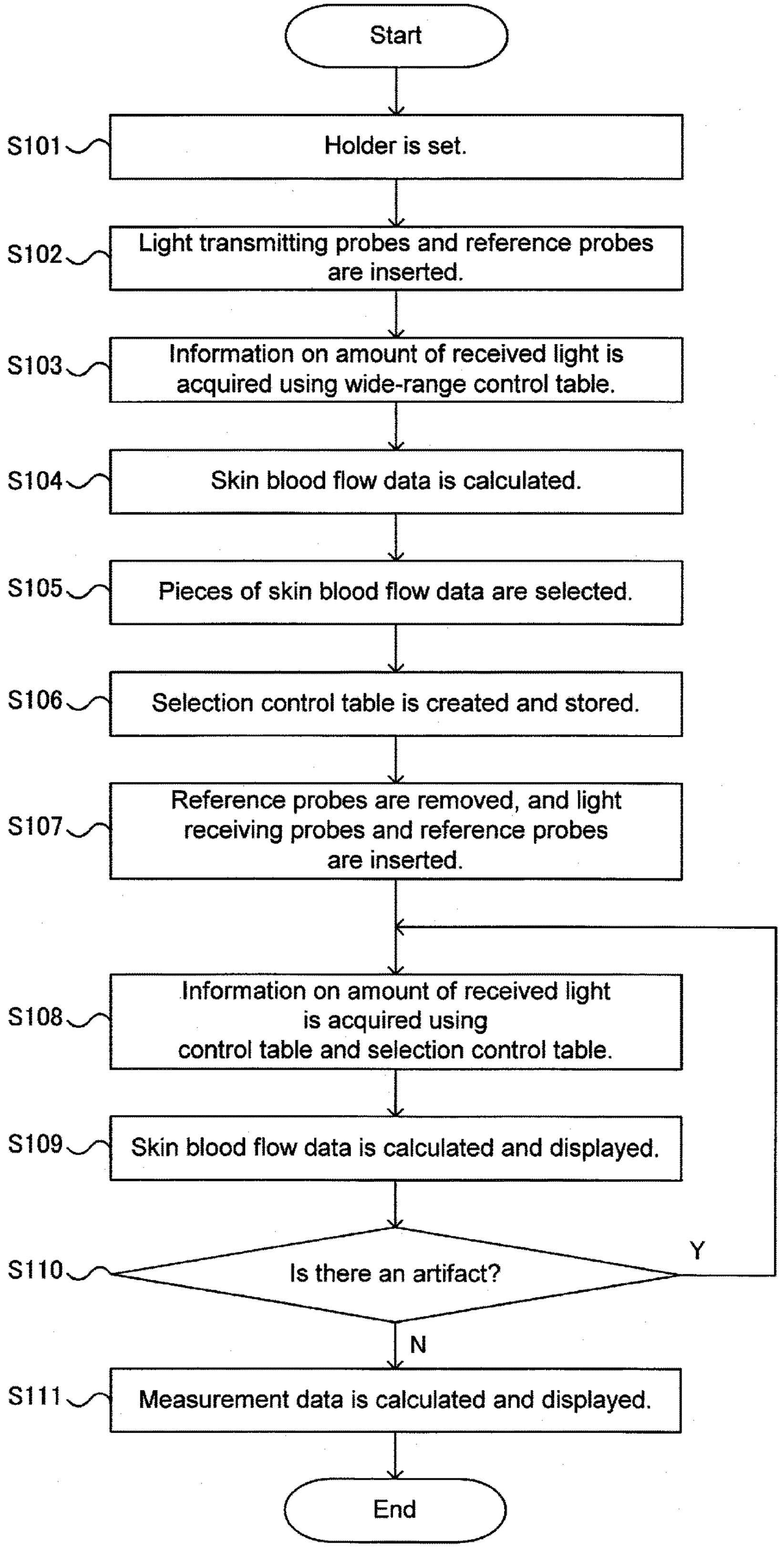
FIG. 8 is a flow chart showing an example of a method for using an optical biometric apparatus.
Figure 9A:
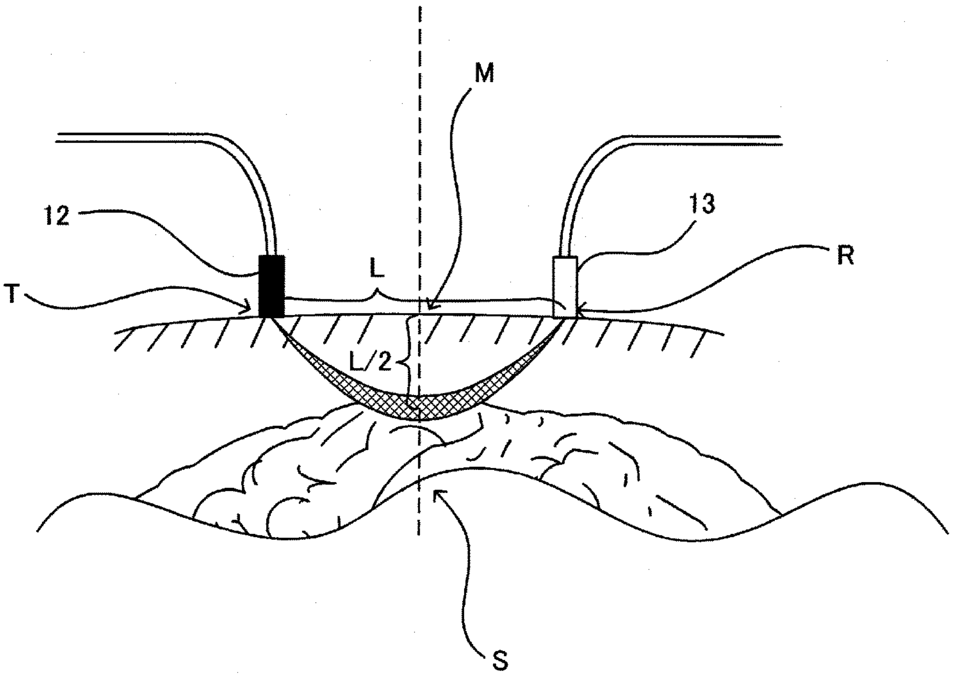
FIGS. 9(*a*) and 9(*b*) are diagrams showing the relationship between a measurement point and a pair of a light transmitting probe and a light receiving probe.
Figure 9B:
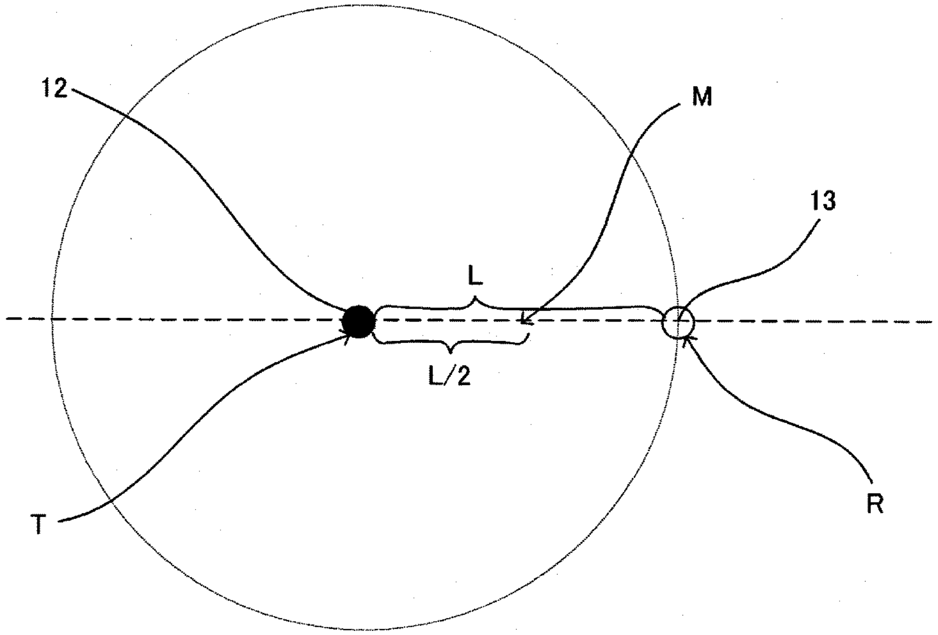
Figure 10:
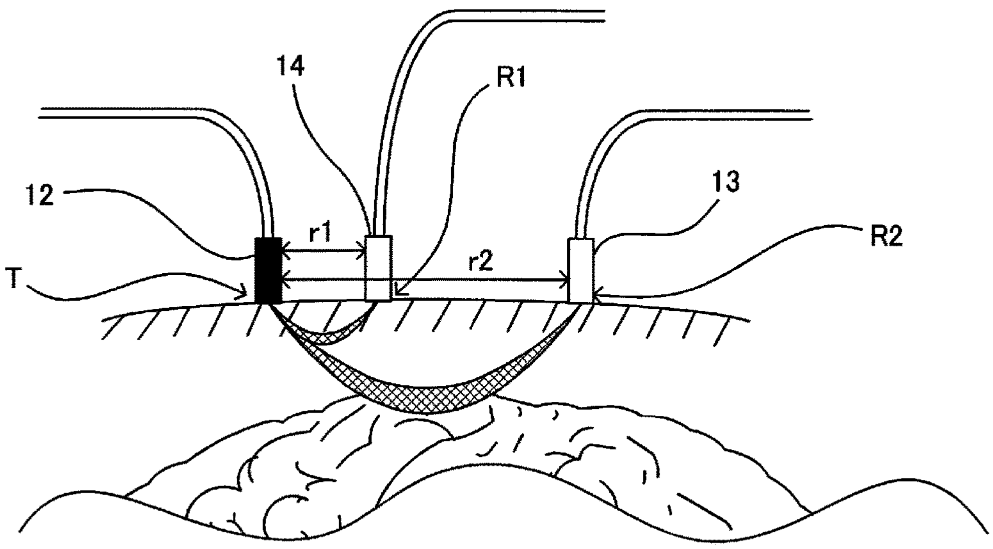
FIG. 10 is a cross-sectional diagram showing the relationship between a measurement point and a reference probe having a short distance vis-à-vis a light transmitting probe as well as between the measurement point and a light receiving probe having a long distance vis-à-vis the light transmitting probe.
Figure 11:
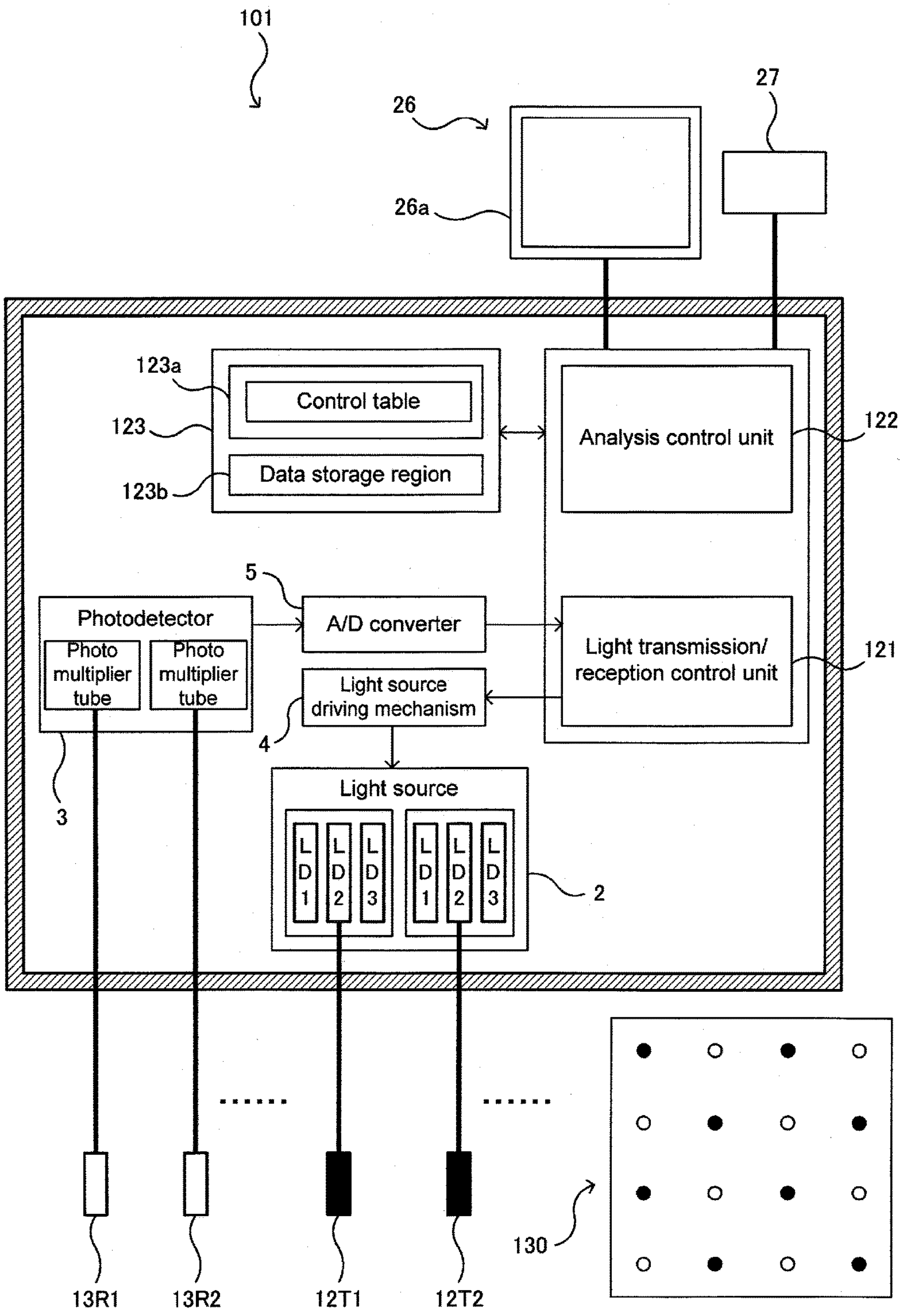
FIG. 11 is a block diagram schematically showing an example of the configuration of a conventional near-infrared spectrometer.
Figure 12:
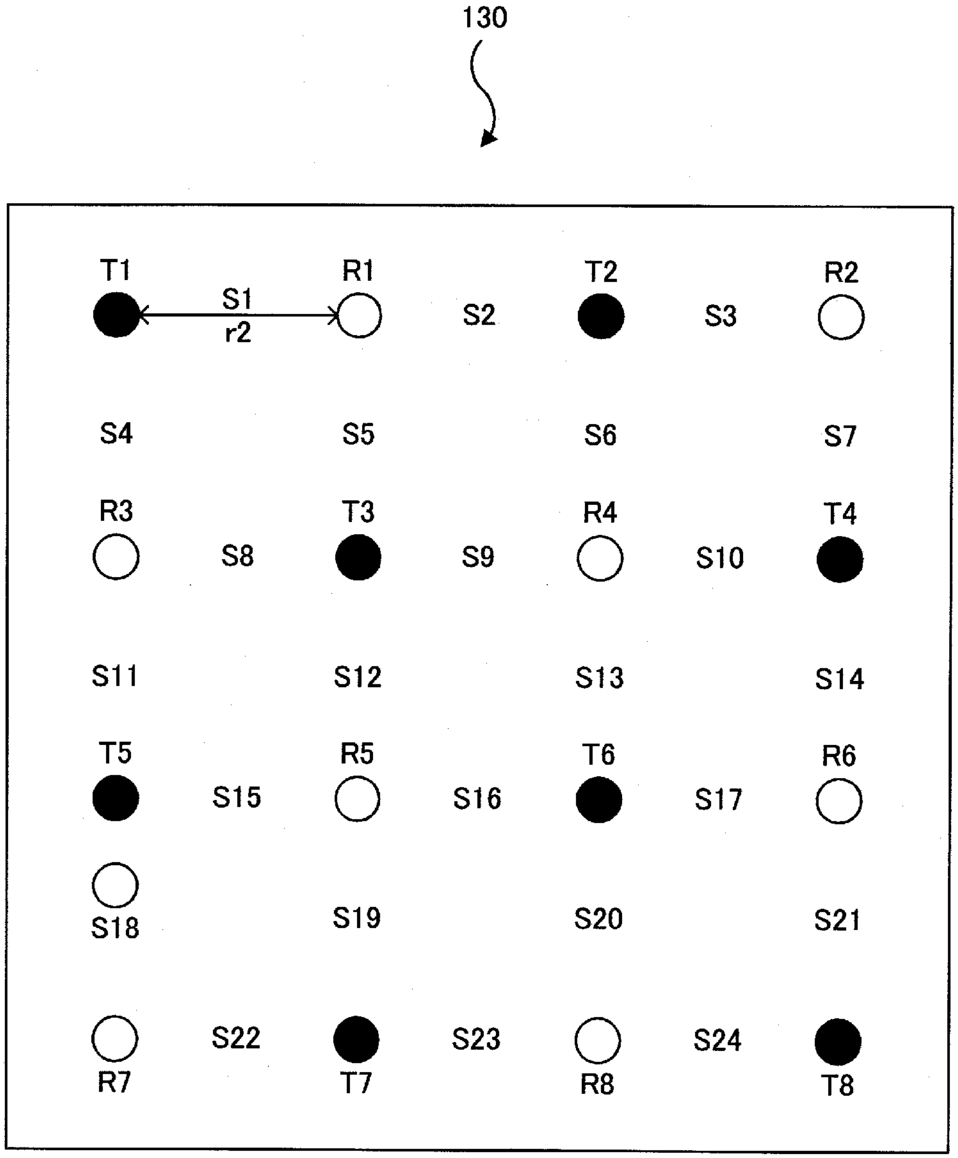
FIG. 12 is a plan diagram showing an example of a holder into which eight light transmitting probes and eight light receiving probes are inserted.

Next, a method for using the optical biometric apparatus 1 is described. FIG. 8 is a flow chart showing an example of a method for using the optical biometric apparatus 1.

First, in the process of step S101, the holder 30 is placed on the surface of the scalp of a subject.

Next, in the process of step S102, eight light transmitting probes $\mathbf{12}_{T1}$ to $\mathbf{12}_{T8}$ are inserted into through holes T1 to T8, and at the same time, eight light receiving probes $\mathbf{13}_{R1}$ to $\mathbf{13}_{R8}$ are inserted into through holes B1 to B8. At this time, the light receiving probes $\mathbf{13}_{R1}$ to $\mathbf{13}_{R8}$ are inserted into the through holes B1 to B8 so as to be used as reference probes $\mathbf{14}_{B1}$ to $\mathbf{14}_{B8}$. That is to say, a pretest and a main test are carried out, and therefore, the light receiving probes $\mathbf{13}_{R1}$ to $\mathbf{13}_{R8}$ are used as the reference probes $\mathbf{14}_{B1}$ to $\mathbf{14}_{B8}$.

Next, in the process of step S103, the unit for acquiring first information on the amount of received light 25 outputs a drive signal for transmitting light to one light transmitting probe 12 at a predetermined time to the light source driving mechanism 4 on the basis of the wide-range control table, and at the same time allows the photodetector 3 to detect eight pieces of first information $\Delta A1_n(\lambda_1)$, $\Delta A1_n(\lambda_2)$ and $\Delta A1_n(\lambda_3)$ (n=1, 2 . . . 8) on the amount of light received by the reference probes $\mathbf{14}_{B1}$ to $\mathbf{14}_{B8}$ (pretest step).

Next, in the process of step S104, the analysis control unit 22 finds the product [oxyHb] of the change in the concentration of oxyhemoglobin and the optical path length, the product [deoxyHb] of the change in the concentration of deoxyhemoglobin and the optical path length, and the product ([oxyHb]+[deoxyHb]) of the change in the concentration of total hemoglobin and the optical path length as eight pieces of skin blood flow data on the basis of the eight pieces of first information on the amount of received light $\Delta A1_n(\lambda_1)$, $\Delta A1_n(\lambda_2)$ and $\Delta A1_n(\lambda_3)$ (n=1, 2 . . . 8) using the relational expressions (1), (2) and (3), and displays the results on the monitor screen 26*a*.

Next, in the process of step S105, the doctor, technician or the like selects a desired number of measurement points and the skin blood flow data on those points from among the eight pieces of skin blood flow data through an input operation on the image displayed on the monitor screen 23*a* using the keyboard 27 (selection step).

Next, in the process of step S106, the selection control table creation unit 24 creates a selection control table for acquiring X pieces of skin blood flow data and stores the selection control table in the control table storage region 23*a*.

Next, in the process of step S107, eight reference probes $\mathbf{13}_{R1}$ to $\mathbf{13}_{R8}$ are removed from the through holes B1 to B8 and are inserted into the through holes R1 to R8, and at the same time, two reference probes 14*a* and 14*b* are inserted into the through holes B3 and B4.

Next, in the process of step S108, the light transmission/reception control unit 21 outputs a chive signal for transmitting light to one light transmitting probe 12 a predetermined time to the light source driving mechanism 4 on the basis of the control table and the selection control table, and at the same time allows the photodetector 3 to detect the 24 pieces of second information $\Delta A1_x(\lambda_1)$, $\Delta A1(\lambda_2)$ and $\Delta A2(\lambda_3)$ on the amount of light received by the light receiving probes $\mathbf{13}_{R1}$ to $\mathbf{13}_{R8}$ and the reference probes 14*a* and 14*b*, and the two (X) pieces of first information on the amount of received light $\Delta A1_x(\lambda_1)$, $\Delta A1_x(\lambda_2)$ and $\Delta A1_x(\lambda_3)$ (x=1, 2) (main test step).

Next, in the process of step S109, the analysis control unit 22 finds the product [oxyHb] of the change in the concentration of oxyhemoglobin and the optical path length, the product [deoxyHb] of the change in the concentration of deoxyhemoglobin and the optical path length, and the product ([oxyHb]+[deoxyHb]) of the change in the concentration of total hemoglobin and the optical path length as two pieces of skin blood flow data from the intensity of the light that has passed through the optical paths having respective wavelengths (wavelength of light absorbed by oxyhemoglobin and wavelength of light absorbed by deoxyhemoglobin) on the basis of the two pieces of first information on the amount of received light $\Delta A1_x(\lambda_1)$, $\Delta A1_x(\lambda_2)$ and $\Delta A1_x(\lambda_3)$ (x=1, 2) using the relational expressions (1), (2) and (3), and displays the results on the monitor screen 26*a*.

Next, in the process of step S110, the doctor, technician or the like observes the two pieces of skin blood flow data and determines whether or not there is an artifact. In the case where it is determined that there is an artifact, the process returns to step S108. That is to say, the main test is carried out again.

Meanwhile, in the case where it is determined that there is no artifact, in the process of step S111, the analysis control unit 22 finds the product [oxyHb] of the change in the concentration of oxyhemoglobin and the optical path length, the product [deoxyHb] of the change in the concentration of deoxyhemoglobin and the optical path length, and the product ([oxyHb]+[deoxyHb]) of the change in the concentration of total hemoglobin and the optical path length as 24 pieces of measurement data from the intensity of the light that has passed through the optical paths having respective wavelengths (wavelength of light absorbed by oxyhemoglobin and wavelength of light absorbed by deoxyhemoglobin) on the basis of the 24 pieces of second information on the amount of received light $\Delta A2(\lambda_1)$, $\Delta A2(\lambda_2)$ and $\Delta A2(\lambda_3)$ using the relational expressions (1), (2) and (3), and displays the results on the monitor screen 26*a*.

Thus, the present flow chart is completed when the process in step S111 is completed.

As described above, the optical biometric apparatus 1 allows the doctor, technician or the like to carry out a pretest in order to examine eight pieces of skin blood flow data so that a necessary two pieces of skin blood flow data can be selected, and as a result, in the main test, 24 pieces of measurement data can be acquired after only the necessary two pieces of skin blood flow data have been acquired. Thus, 24 pieces of measurement data can be acquired in cases where there are no artifacts as a result of the observation of the necessary two pieces of skin blood flow data.

In addition, the optical biometric apparatus 1 is only provided with eight light transmitting probes 12, eight light receiving probes 13 and two reference probes 14*a* and 14*b* in order to make it possible to acquire 24 pieces of measurement data, and at the same time to acquire necessary skin blood flow data. Accordingly, the optical biometric apparatus 1 does not need to be provided with eight light transmitting probes, eight light receiving probes and eight reference probes, and thus, the cost can be reduced.

Other Embodiments (1) Though the above-described optical biometric apparatus 1 has such a configuration that two pieces of skin blood flow data are selected from among eight pieces of skin blood flow data, other numbers of pieces, for example, three pieces of skin blood flow data, may be selected from among eight pieces of skin blood flow data in the configuration.

(2) Though the above-described optical biometric apparatus 1 has such a configuration that a desired number of measurement points (X) and the skin blood flow data on those points are selected from among eight (N) pieces of skin blood flow data using the keyboard 27, a threshold value or the like may be registered depending on the contents of the skin blood flow data so that a desired number of measurement points (X) and the skin blood flow data on those points can be automatically selected from among eight (N) pieces of skin blood flow data.

INDUSTRIAL APPLICABILITY

The present invention can be applied to an optical biometric apparatus and the like for measuring brain activity noninvasively.

EXPLANATION OF SYMBOLS

1: Optical biometric apparatus (optical biometric system)
12: Light transmitting probe
13: Light receiving probe
14: Reference probe
21: Light transmission/reception control unit
23: Memory (storage unit)
24: Selection control table creation unit
25: Unit for acquiring first information on the amount of received light
30: Holder (light transmission/reception unit)

The invention claimed is:

1. A method for acquiring skin blood flow data using an optical biometric system having a light transmission/reception unit having a number of light transmitting probes placed on a surface of a scalp of a subject and a number of light receiving probes placed on the surface of the scalp, where each light receiving probe is located in a through hole for a light receiving probe that is provided at a point a second set distance r2 away from a light transmitting probe, and a light transmission/reception control unit for acquiring a number of pieces of measurement data on the brain activity in a predetermined range of the brain of the subject by acquiring a number of pieces of second information on the amount of received light ΔA2 between the light transmitting probes and the light receiving probes, where through holes for reference probes into which N reference probes can be placed at points a first set distance r1, which is shorter than the second set distance r2, away from a light transmitting probe are provided in said light transmission/reception unit, the method comprising:

a pretest step of acquiring skin blood flow data on the blood flow in the skin in a wide range of the scalp of said subject by acquiring N pieces of first information on the amount of received light ΔA1 between the light transmitting probes and the reference probes that are placed in said through holes for reference probes, a selection step of selecting X pieces of the first information on the amount of received light ΔA1 from among the N pieces of first information on the amount of received light ΔA1, and a main test step of acquiring skin blood flow data on the blood flow in the skin in a predetermined point on the scalp of said subject by acquiring X pieces of first information on the amount of received light ΔA1 when a number of pieces of measurement data on the brain activity in a predetermined range of the brain of the subject is acquired by acquiring a number of pieces of second information on an amount of received light ΔA2 between the light transmitting probes and the light receiving probes that are placed in said through holes for light receiving probes.

2. The method for acquiring skin blood flow data using an optical biometric system according to claim 1, wherein some of the reference probes attached within the through holes for reference probes are removed and attached within through holes for light receiving probes as light receiving probes in the main test step.

* * * * *